United States Patent [19]

Morgan

[11] Patent Number: 5,510,246
[45] Date of Patent: Apr. 23, 1996

[54] METHOD FOR RAPID QUANTIFICATION OF MICROORGANISM GROWTH

[75] Inventor: Scott D. Morgan, Cottage Grove, Minn.

[73] Assignee: Minnesota Mining and Manufacturing Company, St. Paul, Minn.

[21] Appl. No.: 357,761

[22] Filed: Dec. 15, 1994

Related U.S. Application Data

[63] Continuation of Ser. No. 61,678, May 14, 1993, abandoned.

[51] Int. Cl.$^6$ .............................. C12Q 1/06; G06M 11/02
[52] U.S. Cl. .............................. 435/39; 435/808; 377/10; 382/133
[58] Field of Search ................ 435/39, 808; 364/413.07, 364/413.1; 377/10; 382/6, 47, 133

[56] References Cited

U.S. PATENT DOCUMENTS

| | | | |
|---|---|---|---|
| 3,493,772 | 3/1970 | Daughters, II et al. | 250/222 |
| 3,736,432 | 5/1973 | Sweet | 250/222 |
| 3,764,480 | 10/1973 | Jedlicka et al. | 195/103.5 |
| 3,811,036 | 5/1974 | Perry | 235/92 |
| 3,972,778 | 8/1976 | Cunningham | 195/139 |
| 4,116,775 | 9/1978 | Charles et al. | 195/103.5 |
| 4,118,280 | 10/1978 | Charles et al. | 195/127 |
| 4,456,380 | 6/1984 | Kondo et al. | 356/418 |
| 4,536,239 | 8/1985 | Brighton | 250/339 |
| 4,637,053 | 1/1987 | Schalkowsky | 382/6 |
| 4,700,298 | 10/1987 | Palcic | 364/414 |
| 4,724,543 | 2/1988 | Klevecz | 382/6 |
| 4,896,966 | 1/1990 | Boisseau et al. | 356/442 |
| 4,922,092 | 5/1990 | Rushbrooke | 250/213 |
| 5,003,611 | 3/1991 | Miyake et al. | 382/6 |
| 5,117,467 | 5/1992 | Misaki | 382/6 |

FOREIGN PATENT DOCUMENTS

| | | | |
|---|---|---|---|
| 0301600 | 2/1989 | European Pat. Off. | G01N 21/59 |
| 2603074 | 1/1988 | France | G06F 15/62 |
| 2443410 | of 0000 | Germany | G06M 11/02 |
| 3916804 | 11/1989 | Germany | C12Q 1/06 |
| 59-187777 | 10/1984 | Japan | C12M 1/34 |
| 62-60069 | 3/1987 | Japan | G06F 15/62 |
| 2-6729 | 1/1990 | Japan | G01N 15/14 |
| 1434465 | 10/1988 | U.S.S.R. | G06M 11/02 |
| 2227346 | 7/1990 | United Kingdom . | |
| WO93/14599 | 7/1993 | WIPO | H04N 7/18 |
| WO94/01528 | 1/1994 | WIPO | C12M 1/34 |

OTHER PUBLICATIONS

Belyaev et al., "Characterization of Bacterial Growth On Solid Medium With Image Analysis", *Journal of Biochemical and Biophysical Methods*, 25 (1992) 125–132.
Abstract, JP 2 055 953, Feb. 26, 1990.

*Primary Examiner*—Ralph J. Gitomer
*Attorney, Agent, or Firm*—Gary L. Griswold; Walter N. Kirn; Paul W. Busse

[57] ABSTRACT

Changes in specified indicia of colony growth in the early stages of incubation are monitored to provide the early detection and enumeration of colonies in the growth medium. Data from images collected at different times is processed to enhance the detection of subtle changes in the specified indicia of colony growth and provide an early indication of the number of colonies present in the growth medium.

9 Claims, 6 Drawing Sheets

METHOD FOR RAPID QUANTIFICATION OF MICROORGANISM GROWTH

This is a continuation of application No. 08/061,678, filed May 14, 1993, now abandoned.

FIELD OF THE INVENTION

The present invention relates to automated counting of microorganism colonies on an inoculated surface. More particularly, the method of the present invention provides for early detection and counting of microorganism colonies on an inoculated surface by detecting early changes in specified indicia of colony growth.

BACKGROUND OF THE INVENTION

Different methods and devices are known for counting microorganism colonies grown in, for example, petri dishes. Manual counting of colonies by trained laboratory personnel is well known. That method has many disadvantages including the cost associated with the use of skilled technicians to perform the time-consuming chore of manual counting, as well as the limited accuracy in the counts achieved.

Those problems are further compounded when early detection of microorganism colonies in cultured petri dishes is required. Early detection is very useful for manufacturers because it allows the manufacturer to cease production of what would likely be scrap or waste products, also avoiding further processing of those contaminated products which would result in additional expenses.

One example of a beneficial application of early detection is in testing for microorganisms in food products. Samples of the products are taken and culturing devices are inoculated and incubated for a period of 24 or more hours to obtain counts of microorganism colonies indicating the level of contamination in the product. If the samples indicate excessive contamination, the product must often be discarded. Reliable early detection and quantification of excessive contamination in the range of 6 to 12 hours after inoculation would be welcomed by manufacturers because it would allow them to identify contaminated products early in processing, thereby avoiding additional expenses incurred in processing product that will be discarded and possibly contaminating additional product by running it through contaminated processing equipment.

Although technicians can perform early detection of excessive contamination using culturing devices, there are disadvantages associated with having technicians provide the counting as opposed to automated detection systems.

An important indicator of early colony growth is the rate of growth or change between successive readings of the culturing devices. It is difficult, if not impossible, for a human technician to accurately gauge the rate of growth or to distinguish the minute changes in growth indicia for what could be hundreds of culturing devices, all of which would be monitored by a single technician. It is also typically more expensive to employ technicians to provide colony counts and, given the additional difficulties associated with early detection, those costs could be expected to be even higher still.

Automated systems for counting microorganism colonies are known but are typically directed at producing total counts of fully incubated growth media, i.e., growth media that have been incubated for 24 hours or more. The known systems can be separated into two basic categories.

The first category includes systems employing cameras or video equipment in conjunction with hard wired circuits or digital computers to count the number of colonies in a culturing device or detect overall contamination levels in culturing devices by measuring total light absorption of the culturing devices. Examples of such systems are described in EP Publication No. 0 301 600; U.S. Pat. No. 3,811,036 to Perry; U.S. Pat. No. 5,003,611 to Miyake et al., and French Publication No. 2 602 074.

Those systems are designed to count colonies in culturing devices which have been incubated for a longer period of time such as 24 or more hours as discussed above. The systems are not designed to provide reliable early counts of the colonies on a culturing device.

The second category of automated counting systems typically uses an array of photodetectors and hard wired circuitry to perform the counting process. These systems typically provide signals which indicate that a colony is either existing or not existing. They do not supply information regarding the intensity of the colonies or their rate of growth between intervals. Because the systems are unable to provide indications of the varying intensifies of the indicators used to determine colony growth, they are not particularly useful for the early detection and counting of microorganism colonies.

Because the known automated counting systems are designed to count colonies on a fully incubated culturing device, detect overall contamination levels in culturing devices by measuring total light absorption of the culturing devices or merely count colonies without measuring the intensity of the indicia of colony growth, no automated method for producing a reliably accurate early count of microorganism colonies is known.

Reliable early detection and counting, however, can be accomplished by monitoring minute changes in one or more specified indicia of colony growth. Such indicia can include indicators which are not visible such as the acid or enzymes produced by microorganism colonies during growth and other indicia which may or may not be visible to the naked eye.

As a result, a need exists for a method of providing early detection and quantification of microorganism colonies in inoculated culturing devices by detecting early changes in specified indicia of colony growth.

SUMMARY OF THE INVENTION

The method of the present invention relies on changes in specified indicia of colony growth in the early stages of incubation to provide the early detection advantages of the present invention. Data collected during the imaging steps is processed according to the method of the present invention to enhance the detection of subtle changes in the specified indicia.

The culturing devices used in the preferred method according to the present invention produce a specific color change caused by the presence of acid formed by microorganism colonies during growth. It is that color change which is relied on early in the incubation period as the indicator of colony growth.

The method of collecting data and processing it described in the present invention provides specific advantages for early detection of colony growth which are not available to known automated systems and detection methods and which also cannot reasonably be duplicated by human technicians.

In the preferred method, acid regions surround each microorganism colony and the color change associated with each acid zone is detected using sensitive video equipment. The collected data is then processed according to the image processing method of the present invention to provide reliable, early quantification of microorganism colonies.

These and other various features and advantages of the method according to the present invention will be apparent upon a reading of the detailed description and associated Drawings below.

DETAILED DESCRIPTION OF THE PREFERRED METHODS

A description of the preferred and alternate methods according to the present invention follows. Reference is made in the description to FIGS. 1–8 which illustrate various features of the preferred and alternate methods.

Figure 1:
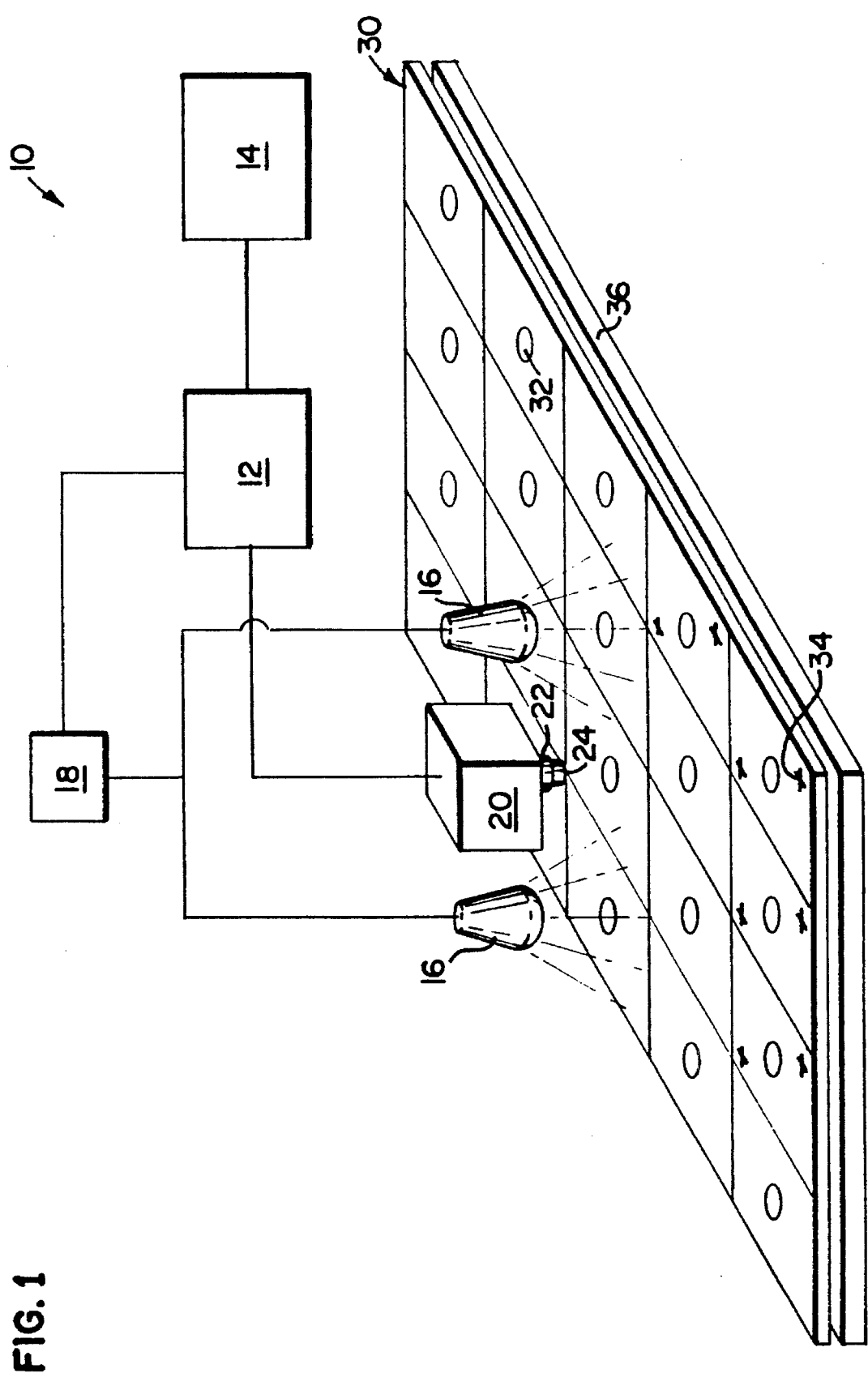
FIG. 1 is a schematic diagram of a preferred embodiment of the image processing system for practicing the method according to the present invention.

FIG. 1 is a schematic diagram illustrating the components of a preferred system to practice the preferred method according to the present invention. As illustrated, the system 10 includes a main processor 12 and associated output device 14 such as a video display and/or printer. Main processor 12 controls power source 18 which controls light sources 16. The main processor 12 also controls a video camera 20 which includes a lens 22 and filter attachment 24. Located below camera 20 is a carrier 30 designed to hold a plurality of culturing devices 32 on which microorganisms are grown.

The lights 16 used to illuminate the upper surface of the carrier 30 and culturing devices 32 are preferably standard linear 15 watt fluorescent light bulbs supplied by General Electric, although many other light sources could be substituted as desired. One contemplated alternate light source would be circular ring-shaped fluorescent bulbs.

Power source 18 is a lamp controller which controls the electrical energy delivered to the lights 16 to provide continuous intensity, ripple-free lighting. The preferred power source 18 supplies electrical energy to the fluorescent light bulb 16 at a frequency of 50 kHz. The preferred power source is a Mercron FX0416-2, available from Mercron, located in Richardson, Tex.

The camera 20 used to practice the preferred method according to the present invention is a model number MCD220 from Spectrasource Instruments, located in Westlake Village, Calif. This camera 20 is peltier cooled in order to minimize thermal noise and provides images to the main processor 12 with 12 bits per pixel and has a resolution of 192 by 165 pixels. The preferred lens 22 is a standard C-mount zoom lens compatible with the preferred camera 20. The lens 22 is adjusted to obtain focus in the desired field-of-view.

The main processor 12 is preferably an IBM compatible PC with a 486 processor, although any suitable microprocessor with sufficient computing capacity and ability to control and retrieve data could be substituted.

Because the preferred method involves the detection of specific wavelengths of reflected light, lens 22 is also preferably supplied with a pair of band-pass filters 24 which can be interposed between the camera 20 and the culturing devices 32 to filter the light reflected from the culturing devices 32. In the preferred method, the band-pass filters 24 are available from Corion, located in Holliston, Mass.

The preferred filters used to practice the preferred methods are a red filter which exhibits a spectral peak at 650 nm and has a bandwidth of 40 nm. The second preferred filter is a green filter which has a spectral peak at 550 nm and a bandwidth of 40 nm. The bandwidth of the filters is chosen to minimize the integration time of the camera 20, while optimizing the signal-to-noise ratio, i.e., contrast, for imaging.

As discussed below, the choice of filters 24 is dependent upon the characteristics exhibited by colonies present on the culturing devices 32 and substitution of alternate filters (or the use of no filters at all) to obtain usable images based on the specified indicia of colony growth. Ultimate filter selection will be well known to those skilled in the art and will not be described further.

The carrier 30 designed to hold a plurality of culturing devices 32 is preferably formed of an opaque material. In the preferred embodiments, the opaque material either corresponds to the background color of the areas imaged on each culturing device 32 or is simply black to minimize blooming in the images.

The use of a carrier 30 including a plurality of culturing devices is advantageous in that the system 10 can monitor the plurality of culturing devices 32 without handling by the operators which can produce errors in positioning and/or additional contamination of the culturing devices 32 from handling. The carrier 30 also prevents displacement of the culturing medium which could lead to erroneous results. It will be understood that carrier 30 is, however, optional but is used in the preferred system 10 because of the advantages described above.

In one embodiment, the carrier 30 includes registration marks 34 located proximate the culturing areas in each culturing device 32. The registration marks 34 serve as registration points for the imaging system 10 to provide highly repeatable accuracy between successive images as carrier 30 is moved between data collection times.

Located below carrier 30 is a heating blanket 36 which provides heat to incubate the culturing devices 32. The entire assembly of the carrier 30 and heating blanket 36 is preferably mounted on an x-y table (not shown) for accurate and repeatable movement between data collection points for each of the culturing devices 32 on the carrier 30.

Although the registration marks 34 can be used to provide registration through the imaging equipment, the repeatable positioning of the x-y table is used in place of registration marks 34 to provide registration between data collection points The preferred x-y table provides repeatable positioning which is accurate to less than one pixel width in both the x and y directions.

The preferred system 10 and method of counting microorganism colonies on culturing devices are both designed primarily for disposable culturing devices such as PETRIFILM, available from 3M Company, St. Paul, Minn. Even more particularly, the preferred method according to the present invention is designed for use with a version of PETRIFILM plates used to detect the presence of microorganisms in samples of food or other products. The preferred plates are designed to produce visible color changes in regions of higher pH which surround a growing microorganism colony. In the preferred plates, the color changes are produced by a phenol red coating placed in the culturing area of the plate, which produces a yellow colored area on the red background in response to acid produced by the colonies.

It will, however, be understood that other culturing devices 32, such as the PETRIFILM Coliform Count (PCC) plates or standard petri dishes could be used in place of the preferred plates in the method according to the present invention with appropriate modifications to the imaging system 10.

Figure 2:
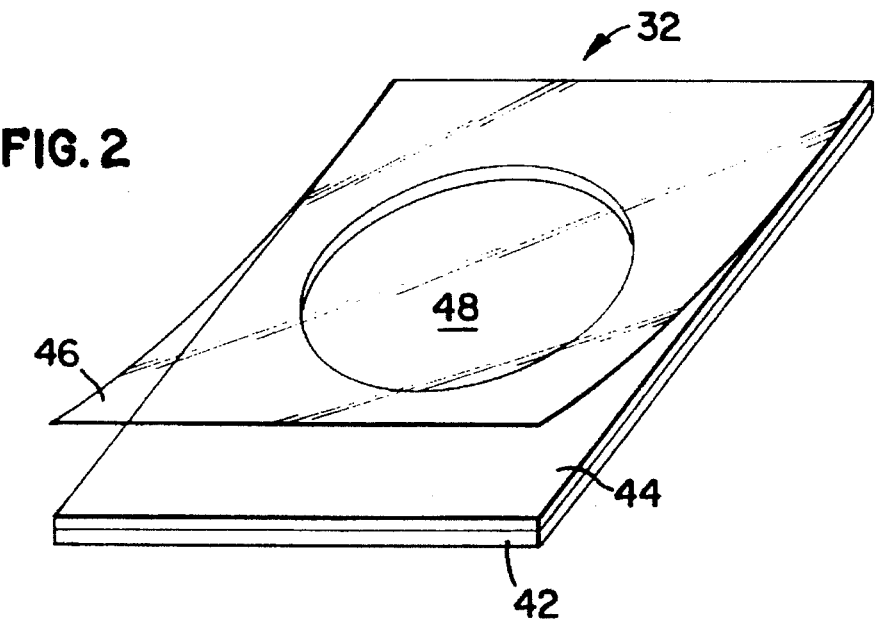
FIG. 2 is a perspective view of a PETRIFILM™ plate used in the preferred method according to the present invention.

One embodiment of a PETRIFILM plate 32 (also referred to above as a culturing device) for use in the preferred method according to the present invention is depicted in FIG. 2. The plate 32 includes a base 42 on which a dam 44 is located. The dam 44 is used to provide a well for the culturing area 48 of plate 32. A flexible cover 46 is preferably attached along one end of plate 32.

For a more complete description of disposable devices for culturing microorganisms such as PETRIFILM plates, the reader is directed to U.S. Pat. No. 4,565,783 to Hansen et al. which is hereby incorporated by reference for its disclosure relating to such devices. The preferred PETRIFILM plate chemistry is more completely described in U.S. Pat. No. 5,364,766 which is hereby incorporated by reference.

The carrier 30 described above is particularly useful for the present commercial embodiment of the PETRIFILM plate 32 as the color of the foam dam 44 is white, which can cause "blooming" or "streaking" of the images produced by the camera 20 due to its high reflectivity relative to the culturing area 48. Blooming can seriously degrade the quality of the image and any later image processing. For that reason, the foam dam is masked using the carrier 30 in the preferred method to minimize blooming.

In use, the culturing devices 32 such as the PETRIFILM plates described above are used to test food samples and other substances for microorganism contamination. In that process, the culturing area 48 of the plate 32 is inoculated with the material to be tested using standard inoculation procedures and the plate 32 is incubated to determine the number of microorganisms located in the tested sample. As the microorganisms grow, they produce acids which cause a chemical reaction in the phenol red indicator located in the preferred plate 32. That change eventually causes yellow areas to appear on the normally red culturing surface 48. The yellow areas can then be counted to determine a level of contamination in the tested sample.

Current testing methods rely on an incubation period of 24 hours to provide an accurate indication of the colony count on each of the culturing devices 32. A particular advantage of the method according to the present invention is the ability to provide early detection of contaminated samples by filtering the collected images and processing them to enhance the color changes produced at the beginning stages of colony growth. By early detection, it is meant that an accurate count of microorganism colonies should be available to the user between six to twelve hours after inoculation.

Although the culturing devices 32 in the preferred method use phenol red indication chemistry on the preferred plates 32, it will be understood that many other culturing devices such as standard petri dishes and agar could be substituted with appropriate modifications to the system 10 and method according to the present invention.

In addition, alternate indicators of microorganism growth could be used to provide early colony counts with the algorithm of the preferred method. Other types of indication systems could include alternate colorimetric indicators such as neutral red, phenol red, bromthymol blue, bromocresol purple, chlorophenol red, bromocresol green, and hydroxypyranine trisulfonic acid (HPTS). Other non-colorimetric indicators such as fluorescence using 4-methyl-umbelliferone (4-MU) could also be used with appropriate illumination, filtering and data collection equipment. Furthermore, although the preferred method relies on visible light, it will be understood that any radiation, including the UV and IR ranges, could be relied on to perform the method of the present invention.

Application of the preferred method using any of the above alternate indicia of colony growth could be implemented with adjustments to the process used to collect the image data. The method of the present invention is, however, designed to apply to any appropriate set of image data collected which is indicative of early colony growth.

The following portion of the description of the preferred method will be separated into a data collection portion and an image processing portion for clarity.

Data Collection

Referring now to FIG. 1, in the preferred method according to the present invention a number of culturing devices 32 are inoculated and placed in the carrier 30 for incubation. In the preferred method, the culturing devices 32 are inoculated with food samples or other similar products which are being tested for contamination by microorganisms.

The preferred early detection system provides a complete colony count within 12 hours of inoculation, more preferably within a six to eight hour period after inoculation. In the preferred method, the culturing devices 32 are initially incubated for approximately 2 hours at which time images are collected from each culturing device 32 using the imaging system 10 described above.

Figure 3:
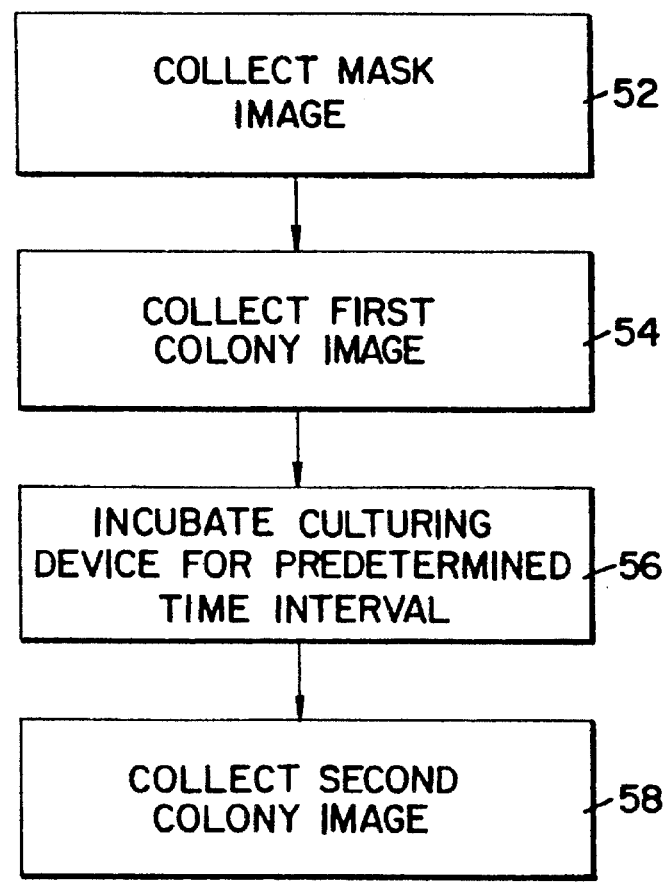
FIG. 3 is a flowchart depicting one preferred embodiment of the data collection portion of the method according to the present invention.

FIG. 3 illustrates the data collection steps of the preferred method according to the present invention. In the method, a mask image is taken (see step 52) to differentiate the culturing area 48 from the mask of carrier 30 or from the foam dam 44 if no mask is used.

The mask image can also be used to exclude noise in the culturing area 48 from being falsely identified as indicia of colony growth. Noise could consist of voids in the culturing media, bubbles, food particles, non-inoculated areas, dust and other objects or conditions which result in a discontinuity in the background of the culturing area 48. To enhance the detection of noise using the mask image, the system 10 preferably includes bottom illumination in addition to the top illumination used for the mask image and the colony images (described below).

Essentially, however, the mask image is used to differentiate the inoculated area 48 from the surrounding carrier 30 or foam dam 44 in the preferred method. It does so by indicating the outer boundary of the inoculated area 48 of each culturing device.

To provide a suitable image, the mask image taken by camera 20 in the preferred method uses a red filter 24 with a peak spectral value of 650 nm and a bandwidth of 40 nm. A red filter is used because the culturing area 48 of the preferred plates 32 is red (because of the phenol red on the plate 32) and, as such, the culturing area 48 appears white when viewed through the preferred red filter.

In the preferred method, the camera 20 takes the mask image using an approximately 3 second integration time with the iris of the lens 22 set appropriately to balance the highest level of contrast in the image with the need to maintain a short integration time.

The determination of an integration time is affected by a number of variables including the intensity of the light source 16 and the bandwidth of the filter 22. The integration time is preferably as short as possible (taking the above considerations into account) to minimize the effect of thermal noise on the CCD in the camera 20.

The preferred camera 20 collects each of the images in a 192×165 pixel array. The preferred camera 20 provides each image with 12 bits per pixel, resulting in each pixel being assigned a value from 0 to 4095 based on the intensity of the light detected at each pixel in camera 20. Pixels with a value of 0 correspond to a black object (returning substantially no light to the corresponding pixel in the camera 20) and pixels with a value of 4095 correspond to a completely white object (completely saturating the corresponding pixel in the camera 20).

Because of the red filtering in the mask image, the mask portion of the carrier 30 appears black to the camera 20 with the pixels generally having values approaching zero. The filtering for the mask image is chosen to enhance the contrast between the culturing area 48 and the mask of carrier 30. As a result there is preferably a distinct difference in pixel values between the culturing area and mask, thereby allowing the system 10 to differentiate between the two areas.

In the preferred mask image pixels with values of 1000–1500 or below are assigned a value of 9999, indicating that they lie on the mask of carrier 30. It will be understood that the value used to determine if a pixel lies on the mask can change based on a variety of factors such as the integration time, filtering, illumination, contrast between the mask and culturing area 48. The exact value can either be predetermined or it can be established for each culturing device 32 through appropriate statistical or other methods based on actual data.

With the pixels corresponding to the mask assigned a value of 9999, the mask image can be used when processing the colony images to indicate which pixels should not be considered as indicating colony growth, no matter what their value. The mask image can also be used to provide registration for the colony images. It can be used for registration by indicating the boundary between the mask (or foam dam 44) and culturing area 48. If the mask image is to be used for registration, the mask is preferably non-circular to allow the system to compensate for rotation between colony images.

Although the system can use the registration marks 34 on the carrier 30 (as described above) or the edges of the culturing area 48, the preferred method relies on the accuracy of the x-y table used to move the carrier 30 below camera 20. The x-y table has repeatable positioning accuracy of less than the dimensions of one pixel in both the x and y directions using the preferred camera 20 and, as a result, additional registration would be redundant.

After the mask image has been collected, a first colony image is collected (see step 54 in FIG. 3) at two hours after inoculation in the preferred method. The first colony image is collected after the culturing device 32 has been incubated for at least an initial period of time to allow the culturing medium to reach a level of relative equilibrium.

In the preferred method, the first colony image is collected after an initial 2 hour incubation period using a green filter 24 placed in front of the lens 22 of camera 20. The green filter preferably has a spectral peak at 550 nm and a bandwidth of 40 nm. The green filter is sensitive to the yellow color produced by microorganism colonies growing on the preferred culturing devices 32 used in the preferred method.

When obtaining the green filtered first colony image the preferred camera 20 is preferably operated using a 40 millisecond integration time with the iris appropriately set to maximize contrast. The same considerations regarding maximizing image contrast and minimizing noise produced by the camera 20 when taking the red filtered mask image also apply when the green filtered first colony image is taken.

In the preferred method, both the red and green filters 24 are mounted in a filter wheel (not shown) which moves them in front of the lens to provide the desired filtering. Such devices are well known to those skilled in the art and will not be described in further detail.

By using the preferred green filter and camera, the first colony image is collected and each pixel in the image is assigned a value between 0 and 4095 based on the intensity of light detected at each pixel in camera 20. As with the red filtered mask image, pixels with a value of 0 correspond to a black object (returning substantially no light to the corresponding pixel in camera 20) and pixels with a value of 4095 correspond to a completely white object (completely saturating the corresponding pixel in the camera 20).

The preferred green filtered image can also be used to identify noise in the culturing area 48. Noise can consist of voids or cracks in the growth medium, bubbles formed during inoculation, particles of inoculant, etc. To minimize voids and cracking in the growth medium, which can appear during incubation, it may be advantageous to provide a humid environment or to seal the edges of the PETRIFILM plate during incubation to limit evaporation from the culturing area 48.

It may also be advantageous to use a polarizing filter in conjunction with the green filter used to collect the colony image as well as the red filter used to collect the mask image. A polarizing filter can reduce the reflections caused by the flexible cover 46 on device 32 (see FIG. 2). For example, a polarizing film may be placed over the light source and a polarizing filter placed over the camera lens. An alternative is to provide an anti-reflective flexible cover 46 for culturing device 32.

Alternately, an additional noise image can be collected at each timepoint using a 450 nm filter with a 40 nm bandwidth (in the preferred method). The same considerations discussed with respect to the mask image and colony image apply to any noise image (e.g., balancing integration time and contrast, etc.). The preferred 450 nm filter is chosen because it is sensitive to changes in gel (i.e., culturing medium) thickness, particularly cracking and voids. The 450 nm filter and image is not, however, sensitive to the color changes used to detect microorganism growth.

After the first colony image is collected, the culturing device 32 is incubated (see step 56 in FIG. 3) for a predetermined time interval after which a second colony image is collected (step 58) using the green filter. The preferred time interval between colony images is 60 minutes. As a result, the second colony image is collected 3 hours after inoculation of the culturing devices 32. The length of the intervals can vary based, for example, on the growth rate of microorganism colonies, sensitivity of the pH indicator, pH of the inoculant, and the sensitivity of the imaging system 10. The lowest frequency (corresponding to the longest interval) which provides acceptable accuracy is preferred as the number of culturing devices 32 that the system 10 can monitor is inversely proportional to the frequency of data collection for each culturing device 32.

As with the first colony image, the second colony image also consists of pixels having values ranging from 0–4095, with the exception of those pixels which have been assigned a value of 9999 in the red filtered mask image taken above.

Image Processing

Figure 4:
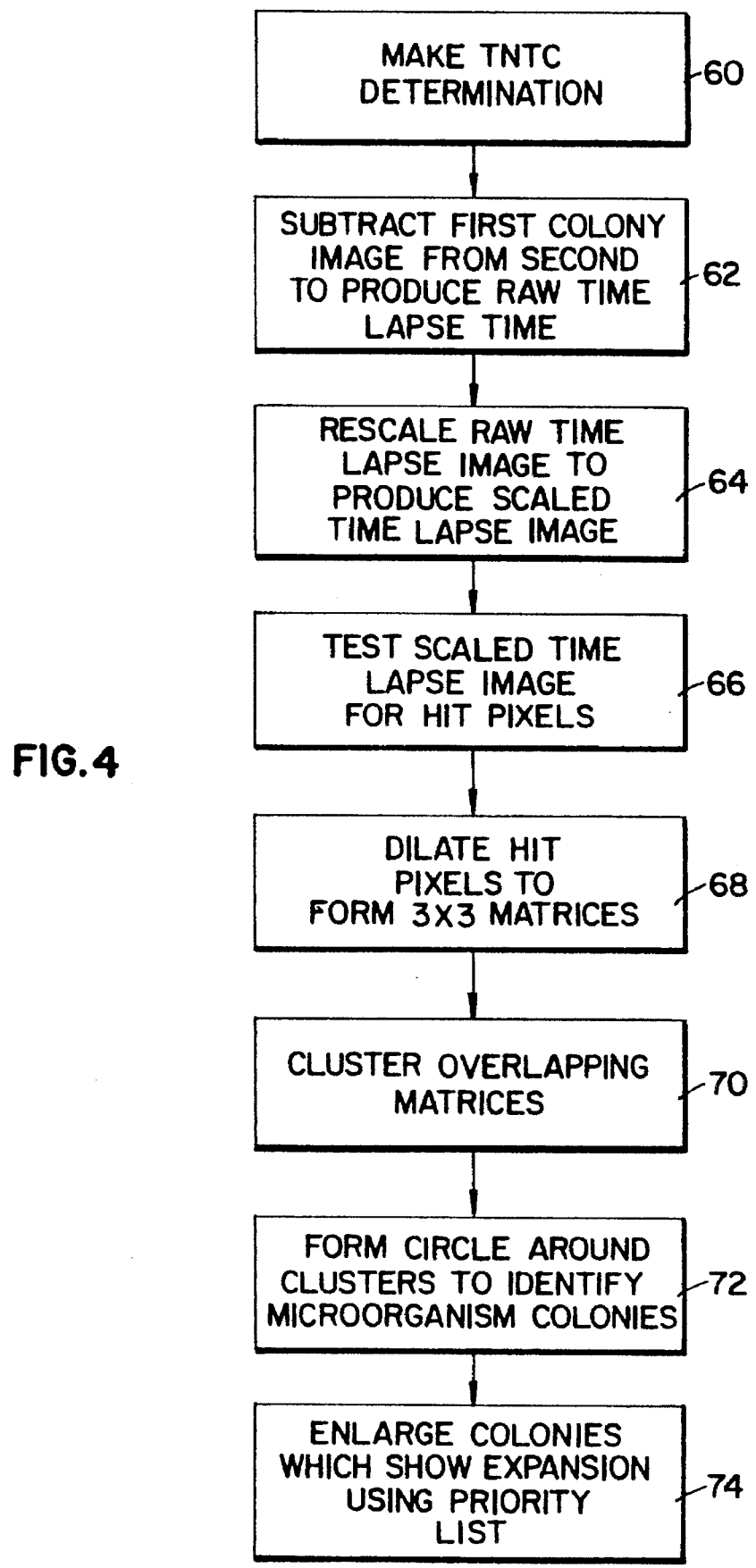
FIGS. 4 & 5 are flowcharts depicting portions of one preferred embodiment of the image processing portion of the method according to the present invention.
Figure 5:
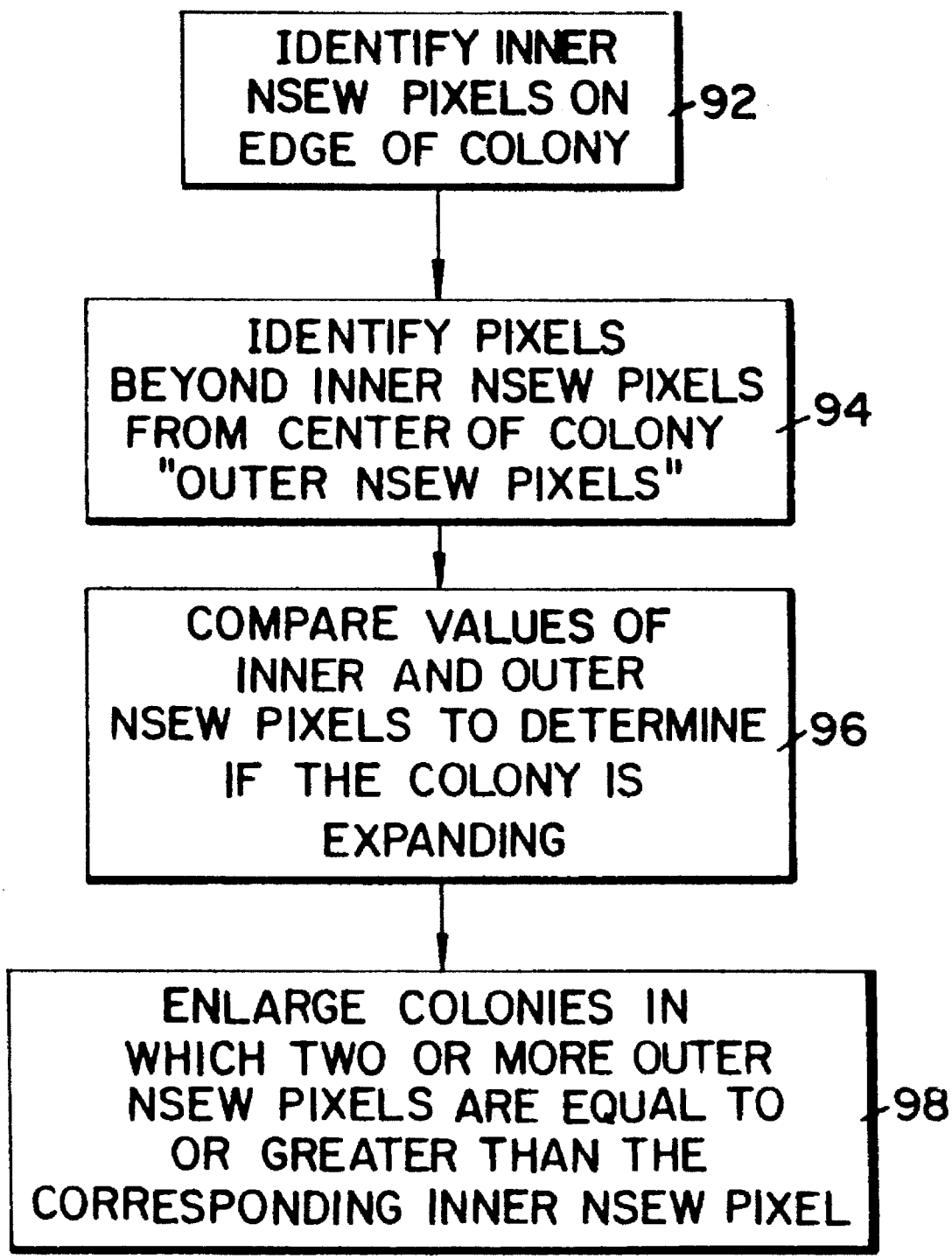

After the first and second colony images have been collected, the image processing portion of the method according to the present invention is used to analyze the images and provide counts of the microorganism colonies appearing on the culturing devices 32. The steps in the preferred image processing method are depicted in the flowcharts of FIGS. 4 & 5.

Although only one iteration of the image processing portion of the preferred method is described below, it will be understood that the method will be used to analyze a series of colony images collected at any number of successive time intervals as discussed above.

The preferred image processing portion of the preferred method begins with the step 60 of determining whether a culturing device will produce a result that is "too numerous to count" (TNTC). The TNTC determination is made by determining a mean pixel value for all of the pixels in the first colony image and a mean pixel value for the second colony image (not including the pixels assigned a value of 9999 in the red filtered mask image).

The mean pixel values for the first and second colony images are compared and, if the difference in the mean pixel values exceeds a predetermined TNTC threshold, a determination is made that the culturing device will produce a TNTC result.

The preferred TNTC threshold is 15%, i.e., if the mean pixel value of the second colony image is 15% or more above the mean pixel value of the first colony image then a TNTC determination is produced. It will be understood that the TNTC threshold value is subject to variation based on a number of factors such as the time interval between the dam collection points, the chemistry of the colony indicators, etc.

Assuming that the first and second colony images do not indicate a TNTC determination, the next step 62 in the image processing portion of the preferred method is the subtraction of the value of each pixel in the first colony image from the corresponding pixel value in the second colony image.

The result of that subtraction step 62 is a raw time lapse image indicating the difference in intensity for each pixel in the colony images collected at successive time intervals corresponding to the times at which the first and second colony images were collected. In the preferred process, pixels assigned a value of 9999 in the red filtered mask image are masked in the raw time lapse image by setting their value to 9999.

The next step 64 is the rescaling of those pixels in the raw time lapse image with values between 50 and 600. The lower value (50) will be referred to below as MINDIFF and the upper value (600) will be referred to as MAXDIFF. The pixels within the MINDIFF and MAXDIFF values are linearly rescaled to have the values between 0 and 4095. In other words, the MINDIFF pixels (having a value of 50) are rescaled and set at 4095 and the MAXDIFF pixels (having a value of 600) are rescaled and set to 0. The pixels with values in between the extremes of the range are linearly scaled to lie within the 0–4095 range.

In addition, those pixels in the raw time lapsed image which show a difference below the MINDIFF value between the first and second colony images are all assigned a value of 4095 (corresponding to white) which, in turn, corresponds to the background of the image. They are assigned to the background because a difference below the chosen MINDIFF value is determined to be within the margin of error (i.e., noise floor) for the pixel values assigned by the system 10. As such, the difference between pixel values between the first and second colony images is small enough to disregard any difference in the pixels' values and assign them to the background of the culturing area.

The pixels having a difference of greater than the MAXDIFF value are all set to 0 (corresponding to black) because, in the preferred method, that difference in pixel values indicates that a significant concentration of acid was produced in that location during the time interval being analyzed. That change would typically be indicative of the center of a growing microorganism colony.

The linear rescaling step 64 described above provides a gray scaled image indicating the changes which occurred in the interval between the first and second colony images. The linearly rescaled image is referred to as the "scaled time lapse image". It is the scaled time lapse image which is then further processed to determine a colony count as discussed below.

An alternative to the linear rescaling of pixel values as described above would be to use a look-up table and assign pixels in the raw time lapse image which fall within the MINDIFF and MAXDIFF range values in the 4095–0 range based on a predetermined table. The use of a look-up table is, however, generally slower for display purposes than the linear rescaling process described above and, as a result, linear rescating is used in the preferred method.

It will be understood that the MINDIFF and MAXDIFF values used to rescale the raw time lapse image can vary based on many factors such as the growth rate of microorganism colonies, pH sensitivity of the indicator, pH of the inoculant, and the sensitivity of the imaging system 10. As such, it will be understood that the range of MINDIFF-MAXDIFF can be adjusted and that an optimum range will generally have to be determined through experimentation.

Furthermore, it will be understood that the linear rescaling step is optional and is used in the preferred method to enhance the display of the time lapse image on a video monitor. As a result, if the system were designed to provide only counts of microorganism colonies without displaying images, the raw time lapse image could be processed without rescaling.

After the scaled time lapse image used in the preferred method has been produced, the next step 66 is to process the scaled time lapse image to determine which pixels are the centers of acid zones and, thus, at the centers of colonies.

Those pixels determined to lie at the centers of colonies will be referred to as "hit pixels". After the hit pixels have been identified, they are dilated 68 to encompass a matrix of pixels in the scaled time lapse image. Those matrices which overlap one another are then clustered 70 and circles are formed 72 around each cluster to identify the boundaries of individual microorganism colonies.

After the first iteration in which only new acid zones corresponding to new colonies are detected, later iterations of the image processing scheme also comprise the step 74 of enlarging previously identified colonies using an enlargement scheme as described in greater detail below.

Figure 6B:
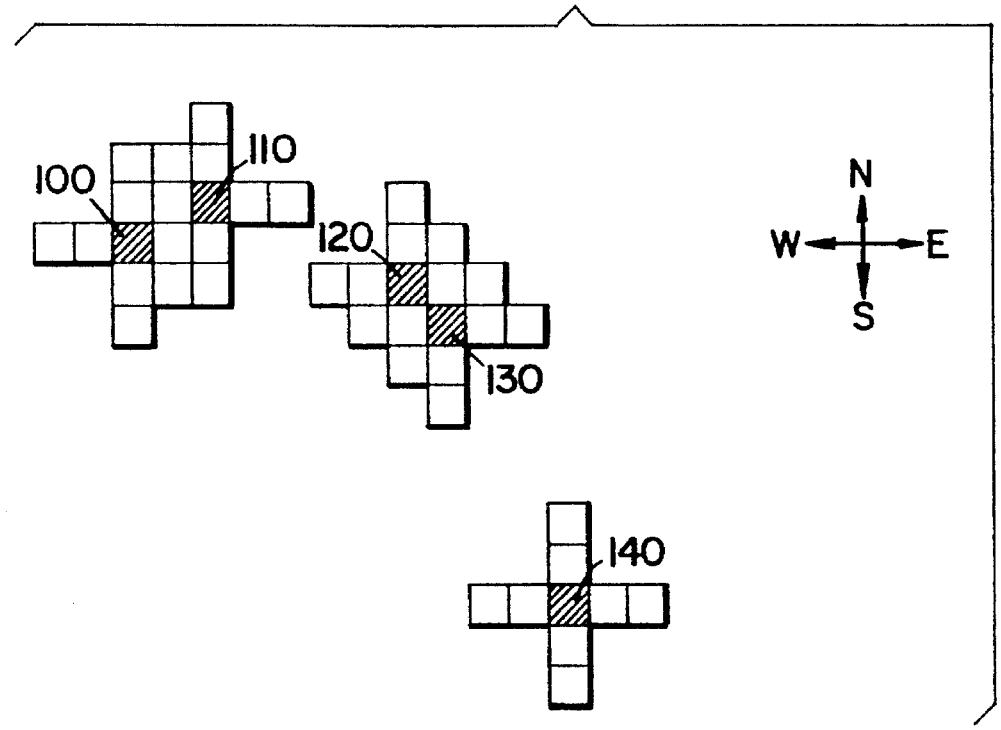
FIGS. 6A & 6B are schematic diagrams of a scaled time lapse image processed according to one preferred method of the present invention.
Figure 6A:
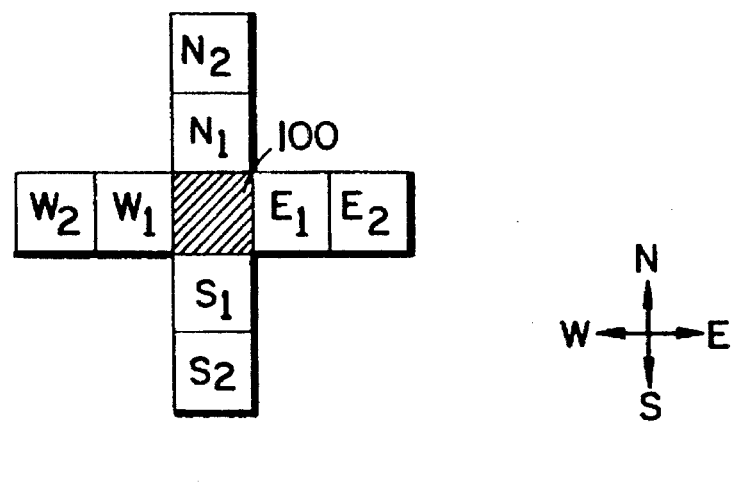

The preferred new colony detection portion of the process is illustrated in both the flow chart of FIG. 4 and schematic diagrams of FIGS. 6A and 6B. The first step 66 is to test every pixel in the scaled time lapse image to determine whether it is a hit pixel. Those pixels assigned a value of 9999 in the mask image are not tested because they lie on the mask of carrier 30 surrounding each culturing area 48.

Furthermore, if noise images are collected (using a 450 nm filter in the preferred method) they are processed similar to the colony images to determine whether any changes have occurred in the culturing medium between data collection points (due primarily to drying). To do so, a first noise image is subtracted from a second noise image to produce a time lapse noise image. Those pixels exhibiting a difference above a "noise" threshold value are assigned a value of 9999, indicating that they are in regions considered to be noise. That image, indicating the position of noise in the culturing area 48, is used in conjunction with the mask image to indicate which pixels should be disregarded when determining microorganism colony counts. In the preferred method, the noise threshold value is 25, although it will be understood that the value is subject to variation and will typically have to be set through experimentation.

Step 66 is described in greater detail below. Essentially, each pixel in the scaled time lapse image is tested to determine whether or not it is the center of a local minimum (which, in the preferred method, corresponds to a local maximum in the raw time lapse image indicative of significant change between the first and second colony images). If it is a local minimum that would indicate that the pixel is at or near the center of a new colony and should be identified as a hit pixel in the preferred method.

Referring to the schematic diagram of FIG. 6A, each pixel 100 is first tested in the preferred method against an acid zone threshold level to ensure that only pixels with a certain level of "darkness" are tested. This filtering helps to minimize the processing requirements as pixels which are at or above the acid zone threshold level of brightness will not generally be located in an acid zone and processing time will not be wasted testing those pixels.

In the preferred method, the acid zone threshold is less than or equal to 3600. The 3600 value was established through experimentation and it is to be understood that it will likely vary based on, for example, the growth rate of microorganism colonies, sensitivity of the pH indicator, pH of the inoculant, and the sensitivity of the imaging system 10.

Pixels in the scaled time lapse image with a value of less than or equal to the acid zone threshold level are sufficiently dark and should be tested to determine whether they are local minima as further described below.

After a pixel 100 has been identified as fitting the above criteria, the four immediate north ($N_1$), south ($S_1$), east ($E_1$), and west ($W_1$) neighbors of pixel 100 are also tested to determine whether they are also sufficiently dark to warrant continuing testing of pixel 100. In the preferred method, those pixels ($N_1$, $S_1$, $E_1$, $W_1$) are tested to determine whether at least three of the four have values which are less than or equal to the acid zone threshold level, i.e., 3600 in the preferred method.

If at least three of those neighboring pixels ($N_1$), $S_1$), $E_1$), $W_1$) do have a value equal to or less than the acid zone threshold level, further testing of center pixel 100 is justified. If this test fails then the pixel 100 will be passed and cannot be labelled as a hit pixel.

If the second criteria described above is met, then all four neighboring pixels ($N_1$, $S_1$, $E_1$, $W_1$) are tested again to determine whether they are equal to or greater than the value of the center pixel 100. If all four immediate neighbors ($N_1$, $S_1$, $E_1$, $W_1$) have values equal to or greater than the value of the center pixel 100, then it is determined that the center pixel 100 is the darkest pixel of those tested and is, therefore, a local minima which could correspond to the center of a colony. If this test is not passed, then pixel 100 cannot be labelled as a hit pixel.

If all four immediate neighbors have values equal to or greater than the center pixel 100, a further test is performed to ensure that the center pixel 100 is a possible local minimum. This test uses pixels ($N_2$, $S_2$, $E_2$, $W_2$) which are one step removed from the immediate neighbors ($N_1$, $S_1$, $E_1$, $W_1$) of the center pixel 100. Those pixels ($N_2$, $S_2$, $E_2$, $W_2$) are tested to ensure that all four of them have values equal to or greater than their corresponding immediate neighbors ($N_1$, $S_1$, $E_1$, $W_1$), which border on the center pixel 100.

If at least one of the pixels ($N_2$, $S_2$, $E_2$, $W_2$) has a value equal to or greater than its corresponding immediate neighbor ($N_1$, $S_1$, $E_1$, $W_1$), a gradient in pixel values exists from the center pixel 100 outward in at least one direction. That identifies the center pixel 100 as a dark spot and two pixels in at least one direction outward have lesser degrees of darkness.

If all of the above tests are met, all of the neighbors ($N_1$, $S_1$, $W_1$) are again tested to ensure that none of them have a value of 9999. If any one of the tested pixels does have a value of 9999, then the center pixel 100 is not labelled as a hit pixel because it lies on the edge of the culturing area near the mask or near an area of noise, both of which can cause spurious readings resulting in the erroneous determination of local minima.

Although the preferred method relies on testing pixels in the four compass directions as described above, it will be understood that pixels in any other directions could also be tested along the lines of the method as described above and the present invention should not be limited to the precise method described above.

Finally, the distance from the center pixel 100 to the edge of nearest previously identified colony (if any) is computed. If this distance is greater than a predetermined minimum distance (MINDIST), than center pixel 100 can be identified as a hit pixel. If the distance is less than or equal to MINDIST, then center pixel 100 cannot be identified as a hit pixel as it is too close to an existing microorganism colony.

In the preferred method, MINDIST is set at 3.1 pixels. That value was determined through experimentation to minimize false detection of multiple local minima in a colony's expanding acid zone. As such, it will be understood that the MINDIST value can change based on a number of factors such as the rate of colony growth, the sensitivity of the indicator, the sensitivity of the system, the frequency at which images are collected, etc.

If all of the above tests are met, then the center pixel 100 is labelled as a hit pixel in step 66. Referring now to FIG. 6B, which illustrates the results of the above process in which a number of hit pixels 100, 110, 120, 130, 140 have been identified as local minima using the method described above.

Figure 7:
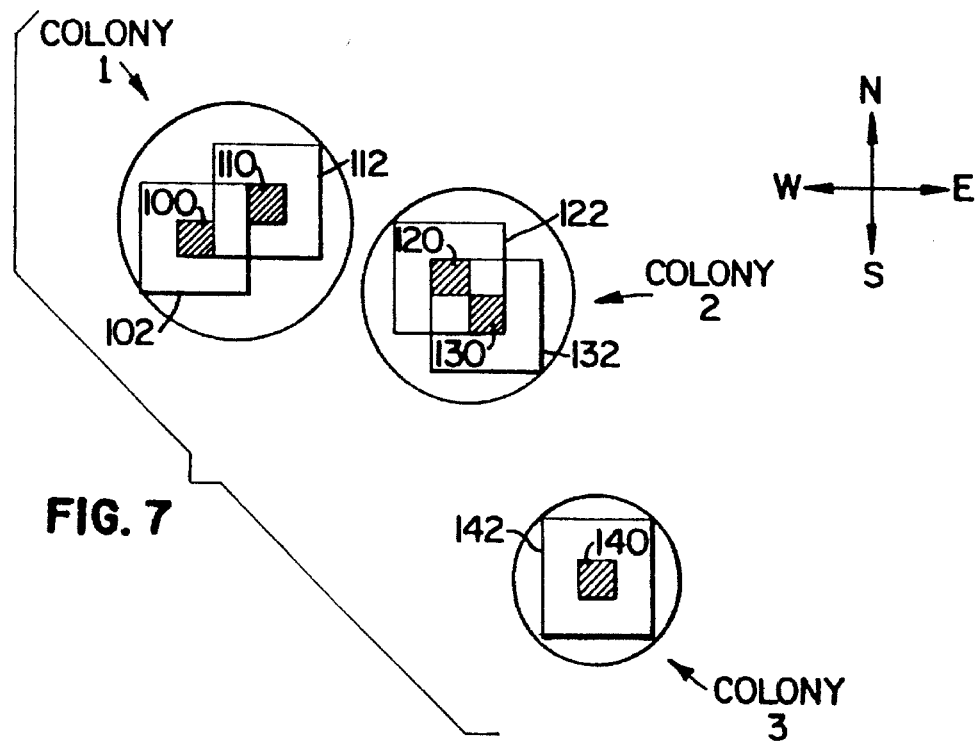
FIG. 7 is a schematic diagram of the image of FIG. 6B which has undergone further processing.

An example of the clustering process which uses hit pixels 100, 110, 120, 130, 140 to identify colonies can be seen in the schematic diagram of FIG. 7. More particularly, pixel 100 is expanded to encompass matrix 102 and pixel 110 is expanded to encompass matrix 112. Likewise, each of the remaining hit pixels 120, 130, 140 is also expanded to a corresponding 3×3 matrix 122, 132, 142, respectively.

As depicted, both matrices 102 and 112 overlap and, as a result, hit pixels 100 and 110 are clustered together. Because a 3×3 matrix is used to perform the dilation, each hit pixel 100, 110, 120, 130, 140 is clustered with its overlapping neighbors (if any) based on 8-neighbor connectedness.

After the hit pixels 100, 110, 120, 130, 140 have been dilated and clustered, a circle is approximated to encompass each cluster. The circles are used to identify the boundaries of identified colonies 1, 2 & 3. It is preferred that the circles be slightly larger than the actual colonies to prevent overcounting of the colonies in an expanding acid zone on a culturing device 32.

At that point, the algorithm has identified microorganism colonies 1, 2 & 3. In the preferred method using 60 minute intervals and beginning imaging at 2 hours, this colony count would be determined at a point 3 hours after incubation (which corresponds to the point at which the second green filtered colony image was collected).

The preferred method also includes a limit on the maximum number of colonies (referred to as MAXNO) which can be identified. A maximum is set because if a number of colonies greater than MAXNO are counted, the culturing device should be indicated as a TNTC device (i.e., too numerous to count). The TNTC determination alerts the operator that a highly contaminated sample has been found. The actual value of MAXNO in the preferred method is 100. It is determined by experimentation and can vary based on many different factors such as the size of the culturing device, resolution of the imaging system, etc.

The preferred image processing method according to the present invention also involves the enlargement of colonies identified in earlier scaled time lapse images. If, for example, colonies 1, 2 & 3 were identified in an initial scaled time lapse image as appearing between hours 2 and 3 (after inoculation), then a subsequent scaled time lapse image would be produced using the green filtered colony images collected at hours 3 and 4. That subsequent scaled time lapse image would then be used to determine whether any of the colonies identified in the initial scaled time lapse image should be enlarged.

The enlargement portion of the process essentially involves testing the pixels on the edge of known colonies (identified in the initial scaled time lapse image) to determine if they indicate colony growth in the time interval used to develop the subsequent scaled time lapse image.

In the preferred enlargement process, a priority list is used to avoid expanding colonies to the point of engulfing other colonies in close proximity. As every new colony is identified as described above, it is added to the bottom of a priority list, which is in numerical order at the start of the process.

For example, colony 1 would be analyzed first to determine whether it was expanding. In the preferred method, the first test includes determining the value of four inner pixels 150a, 152a, 154a & 156a which lie just within the circumference of the circle defining each colony.

The four inner pixels are chosen to lie generally in the NSEW directions from the center of the circle defining colony 1, although it will be understood that any number of pixels lying in any number of directions could be tested.

The next step involves determining the value of each outer pixel 150b, 152b, 154b & 156b, each of which lies just beyond (in a radial direction) the pixels 150a, 152a, 154a & 156a identified above. The outer pixels preferably lie just outside the circumference of the colony being tested.

The values of each pair of pixels identified above are compared to determine whether the colony is expanding in the direction of the identified pixels. If the outer pixels (150b, 152b, 154b & 156b) have a value greater than or equal to their corresponding inner pixels (150a, 152a, 154a & 156a), then the colony is expanding in those directions.

Figure 8:
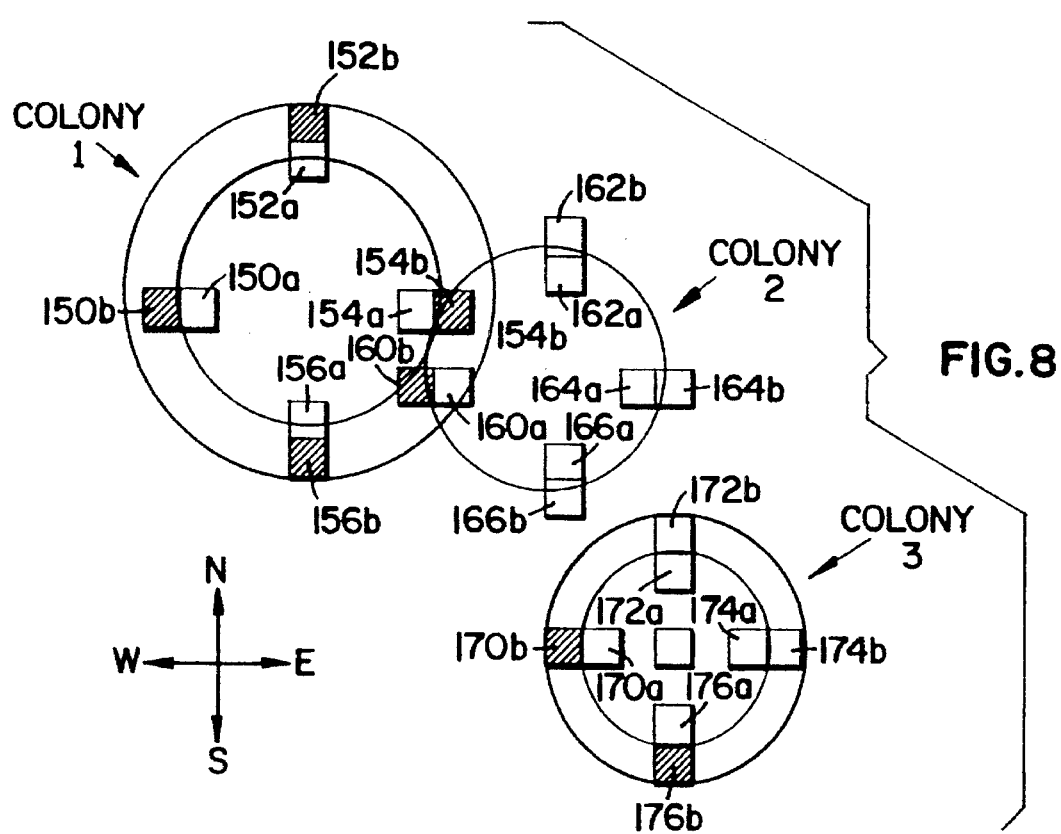
FIG. 8 is a schematic diagram of the image of FIG. 7 which has undergone further processing.

In the preferred method, at least two of the four pairs of pixels must show expansion before the colony is enlarged. As depicted in FIG. 8, colony 1 meets that test because all of the inner and outer pixel pairs show expansion. Colony 1 is, therefore, expanded outward so that its radius is increased by one pixel in the preferred method. This value can be increased depending on many factors such as expected growth rates, intervals between data collection, etc..

At that point colony 1 would be moved to the bottom of the priority list which would now be ordered as 2-3-1. Colony 2 would then be analyzed to determine whether it met the test for enlargement using inner and outer pixels 160a/160b, 162a/162b, 164a/164b & 166a/166b. As indicated in FIG. 8, colony 2 does not meet the test and is not enlarged and, therefore, remains at the top of the priority list.

Colony 3 would then be analyzed to determine if it was expanding. As shown, two pairs of inner and outer pixels 170a/170b and 176a/176b indicate expansion and, as a result, colony 3 is enlarged to encompass the expansion. After enlargement, colony 3 would be moved to the bottom of the priority list, which would now read 2-1-3.

The preferred method also limits the radius of each colony to a value referred to as RADMAX. In the preferred method RADMAX is set at 50 pixels, although it will be understood that the value can change based on many factors such as imaging system resolution, size of the culturing devices, microorganism growth rates, etc.

At this point in the algorithm, the total count would be indicated as 3 colonies. It is considered that only those colonies which expand between intervals, such as clusters 1 and 3, could be identified as confirmed colonies. Colony 2 which has been identified but not yet shown growth could be identified as an unconfirmed colony which could later become confirmed upon indication of growth. In the preferred method, however, all colonies are counted in the total count whether they exhibit enlargement or not.

After indication of a colony count, the system 10 would again reset and incubate the culturing devices 32 for the next time interval, after which the method of collecting a colony image would be repeated along with the steps of processing that image to identify new colonies and expand existing colonies.

It will be understood that even though only one iteration of the above process is described, data collected at different times would be processed in much the same manner as described above. The only change of any significance would be that pixels falling within colonies identified in one iteration of the process (which are used to reach the total count) may be disregarded in later images to speed up the processing of the system.

It is to be understood that even though numerous characteristics and advantages of the present invention have been set forth in the foregoing description, together with details of the method and apparatus used to practice the present invention, the disclosure is illustrative only, and changes may be made in details, especially in matters of details regarding process steps which fall within the principles of the invention to the full extent indicated by the broad, general meaning of the terms in which the appended claims are expressed.

I claim:

1. A method to count microbial colonies growing on an inoculated growth medium adhered to a substantially planar culturing device comprising the steps of:

a) obtaining a filtered mask image of the culturing device to identify pixels in the mask image which lie outside of the inoculated growth medium in order to prevent processing of pixels which lie outside of the growth medium;

b) obtaining a filtered noise image of the culturing device to identify pixels in the filtered noise image having measured intensities outside of a predetermined range of intensities and which lie inside of the growth medium in order to prevent processing of pixels having measured intensities outside of a predetermined range of intensities which lie inside of the growth medium;

c) obtaining a filtered background image of the culturing device to provide background image data which excludes pixels identified in steps a) and b);

d) incubating the inoculated growth medium for a selected time interval;

e) obtaining a first filtered image of the culturing device to provide first image data;

f) processing the background and first image data to produce a difference image wherein the difference image is obtained by taking a difference between the first filtered image data and the background image data;

g) processing the difference image to identify hit pixels which are local maxima, wherein a hit pixel is determined by the steps of:

1) testing a pixel value at a center pixel for compliance with a value;

2) testing at least two neighboring pixel values directly adjacent to the center pixel to insure that the immediate neighboring pixels have values less than the center pixel value;

3) testing pixels adjacent to each of the neighboring pixels of step 2) which are neighbors once removed to the center pixel to insure that they have a value less than the value of an adjacent neighboring pixel; and 4) labeling each center pixel which satisfies the tests of steps 1), 2) and 3) as a hit pixel; and 5) clustering the hit pixels by dilating each of the hit pixels to encompass a matrix and expanding the matrix to encompass hit pixels which overlap one another wherein a number of matrices on the growth medium corresponds to a number of microbial colonies in the growth medium;

h) storing a position and number of matrices which correspond to a count of the microbial colonies in the growth medium; and i) providing a count of the microbial colonies in the growth medium.

2. The method of claim 1 further comprising obtaining a second filtered image to provide second image data, processing the background image data of step c) and second image data to produce a second difference image, wherein the second difference image is obtained by taking a difference between the second image data and the background image data, processing the second difference image by comparing a value of inside hit pixels lying within a perimeter of previously identified matrices with a value of corresponding outside hit pixels adjacent to the inside hit pixels and to hit pixels outside the matrix; expanding matrices having at least two inside hit pixels with a value greater than the corresponding outside hit pixels to provide enlarged matrices and storing the position and number of the enlarged matrices.

3. The method of claim 2 further comprising identifying additional hit pixels according to steps 1) to 5) and adding the position and count of additional matrices to the position and number of enlarged matrices.

4. The method of claim 3 further comprising obtaining additional filtered images collected at successive time intervals.

5. The method of claim 2, wherein the first and second filtered images are detected at light wavelengths of about 550 nm.

6. The method of claim 1 wherein the filtered mask image is detected at light wavelengths of about 650 nm.

7. The method of claim 1, wherein the filtered noise image is detected at light wavelengths of about 450 nm.

8. The method of claim 1 wherein a count of the microbial colonies in the growth medium is too numerous to count if an average pixel value of the first filtered image is greater than a predetermined value of an average pixel value of the filtered background image.

9. The method of claim 8 wherein the predetermined value is about 15% or more of an average pixel value of the filtered background image.

* * * * *

UNITED STATES PATENT AND TRADEMARK OFFICE
CERTIFICATE OF CORRECTION

PATENT NO.: 5,510,246

DATED: April 23, 1996

INVENTOR(S): Scott D. Morgan

It is certified that error appears in the above-identified patent and that said Letters Patent is hereby corrected as shown below:

Col. 9, line 55, "dam" should read --data--.

Signed and Sealed this

Eighth Day of April, 1997

Attest:

BRUCE LEHMAN

Attesting Officer

Commissioner of Patents and Trademarks